United States Patent
Wiebe et al.

(10) Patent No.: US 11,234,653 B2
(45) Date of Patent: Feb. 1, 2022

(54) DETERMINING SENSOR DATA QUALITY BASED ON BIOIMPEDANCE INFORMATION

(71) Applicant: Mad Apparel, Inc., Redwood City, CA (US)

(72) Inventors: Christopher John Wiebe, Burlingame, CA (US); Daniel Blatnik, Sunnyvale, CA (US); Lev Korzinov, San Diego, CA (US); Adnan Aslam, San Jose, CA (US)

(73) Assignee: Mad Apparel, Inc., Redwood City, CA (US)

( * ) Notice: Subject to any disclaimer, the term of this patent is extended or adjusted under 35 U.S.C. 154(b) by 0 days.

(21) Appl. No.: 16/440,045

(22) Filed: Jun. 13, 2019

(65) Prior Publication Data
US 2019/0307404 A1    Oct. 10, 2019

Related U.S. Application Data

(63) Continuation of application No. 15/257,739, filed on Sep. 6, 2016, now Pat. No. 10,362,993.
(Continued)

(51) Int. Cl.
*A61B 5/00* (2006.01)
*G16H 40/67* (2018.01)
(Continued)

(52) U.S. Cl.
CPC .......... *A61B 5/7221* (2013.01); *A61B 5/0022* (2013.01); *A61B 5/0245* (2013.01);
(Continued)

(58) Field of Classification Search
None
See application file for complete search history.

(56) References Cited

U.S. PATENT DOCUMENTS

| 7,801,776 B2 | 9/2010 | Inskeep et al. |
| 8,708,903 B2 | 4/2014 | Tran |

(Continued)

FOREIGN PATENT DOCUMENTS

| WO | WO 2007/064916 A2 | 6/2007 |
| WO | WO 2011/093917 A1 | 8/2011 |
| WO | WO 2015/102156 A1 | 7/2014 |

OTHER PUBLICATIONS

PCT International Search Report and Written Opinion, PCT Application No. PCT/US16/50766, dated Dec. 2, 2016, 21 pages.
(Continued)

*Primary Examiner* — Brian T Gedeon
(74) *Attorney, Agent, or Firm* — Fenwick & West LLP

(57) ABSTRACT

An exercise feedback system determines sensor data quality of an athletic garment based on bioimpedance data. The athletic garment includes sensors that can generate physiological data and bioimpedance data. An athlete wears the athletic garment while exercising. If the sensors have a stable contact with the skin of the athlete, the sensors generate high quality physiological data. However, if the sensors have unstable or no contact with the skin of the athlete, the sensors generate low quality physiological data. The exercise feedback system uses the magnitude and/or variance of the bioimpedance data to determine whether the physiological data is high or low quality. If the physiological data is high quality, the exercise feedback system may generate and provide feedback based on the physiological data for display to the athlete. The exercise feedback system may also use the bioimpedance data to identify defects in the garment during quality assurance tests.

19 Claims, 13 Drawing Sheets

Related U.S. Application Data

(60) Provisional application No. 62/218,207, filed on Sep. 14, 2015.

(51) Int. Cl.

| | | |
|---|---|---|
| *A61B 5/0245* | (2006.01) | |
| *A61B 5/053* | (2021.01) | |
| *A61B 5/276* | (2021.01) | |
| *A61B 5/389* | (2021.01) | |

(52) U.S. Cl.
CPC .............. *A61B 5/276* (2021.01); *A61B 5/389* (2021.01); *A61B 5/486* (2013.01); *A61B 5/6804* (2013.01); *A61B 5/6843* (2013.01); *G16H 40/67* (2018.01); *A61B 5/053* (2013.01); *A61B 2503/10* (2013.01)

(56) References Cited

U.S. PATENT DOCUMENTS

| | | | | |
|---|---|---|---|---|
| 10,362,993 | B2 * | 7/2019 | Wiebe | A61B 5/0245 |
| 2005/0075213 | A1 * | 4/2005 | Arick | A63B 71/0622 |
| | | | | 482/1 |
| 2007/0100702 | A1 * | 5/2007 | Morley | G06Q 30/0603 |
| | | | | 705/27.2 |
| 2010/0231378 | A1 | 9/2010 | Ward | |
| 2014/0031901 | A1 * | 1/2014 | Zhu | A61N 1/36125 |
| | | | | 607/60 |
| 2014/0088394 | A1 * | 3/2014 | Sunderland | A61B 5/0492 |
| | | | | 600/373 |
| 2014/0135593 | A1 | 5/2014 | Jayalth et al. | |
| 2014/0207017 | A1 | 7/2014 | Gilmore et al. | |
| 2015/0148619 | A1 * | 5/2015 | Berg | A61B 5/0024 |
| | | | | 600/301 |
| 2015/0230719 | A1 | 8/2015 | Berg et al. | |
| 2015/0297135 | A1 * | 10/2015 | Shoshani | G06F 1/163 |
| | | | | 600/388 |

OTHER PUBLICATIONS

United States Office Action, U.S. Appl. No. 15/257,739, dated Nov. 26, 2019, 8 pages.

\* cited by examiner

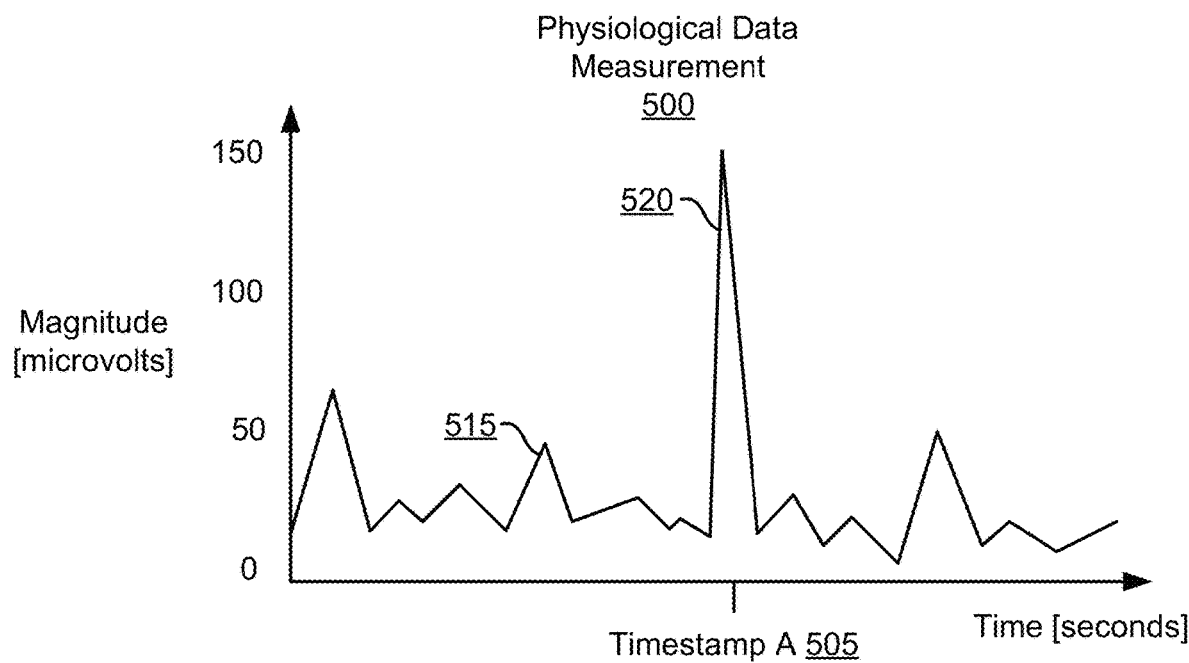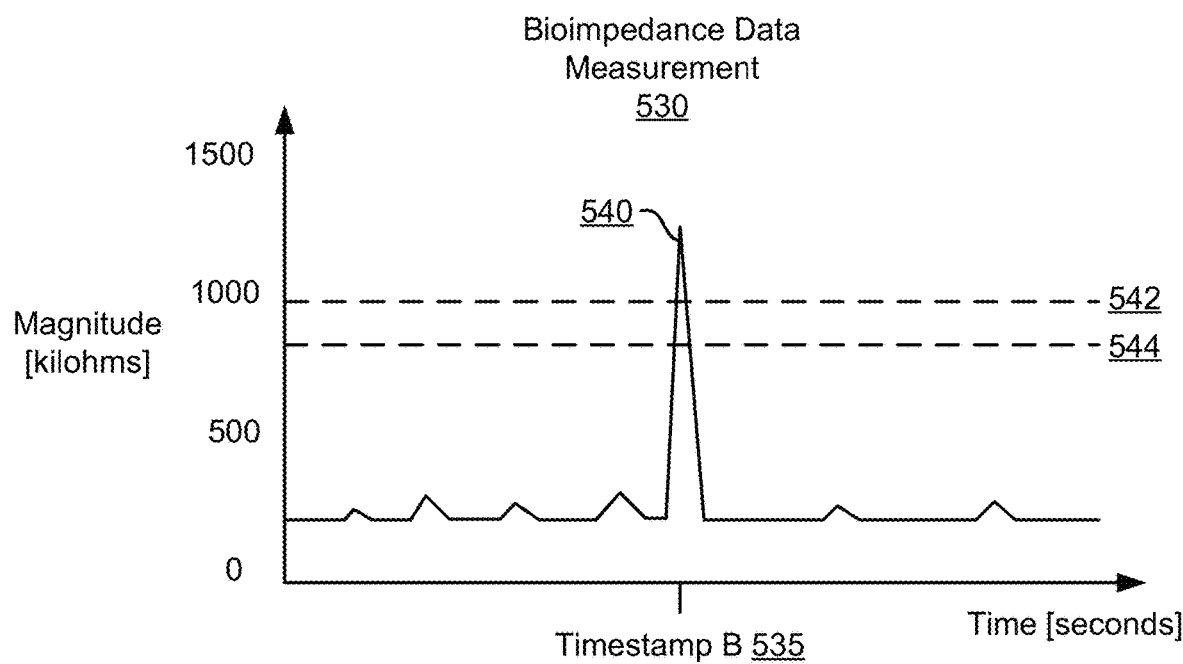
FIG. 5A

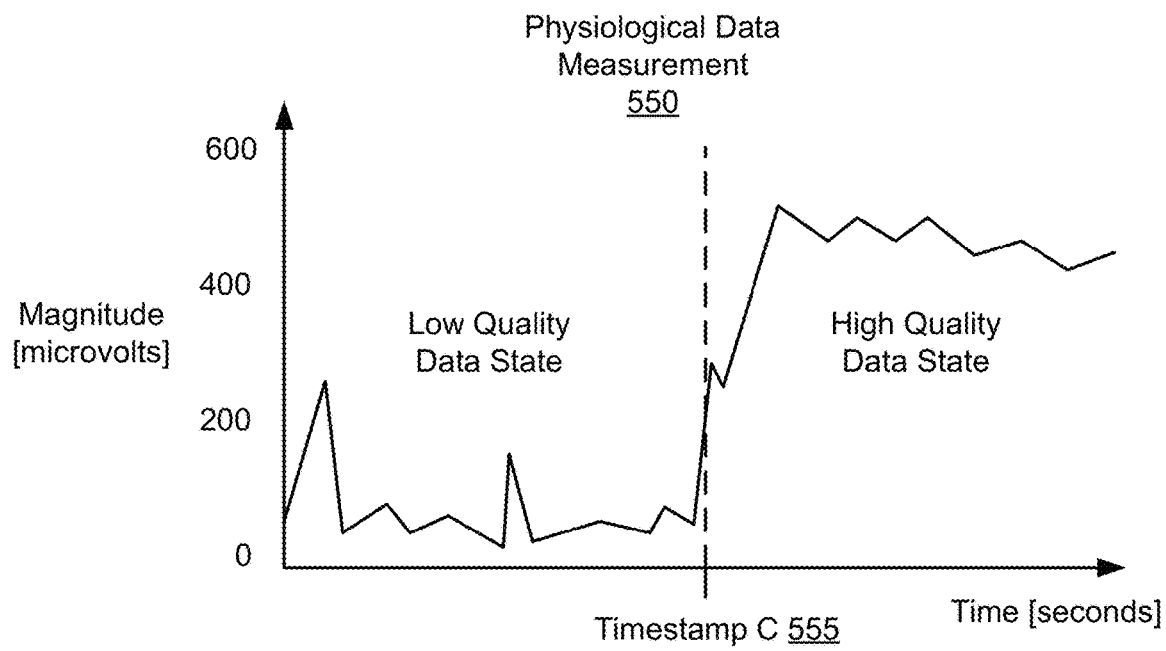
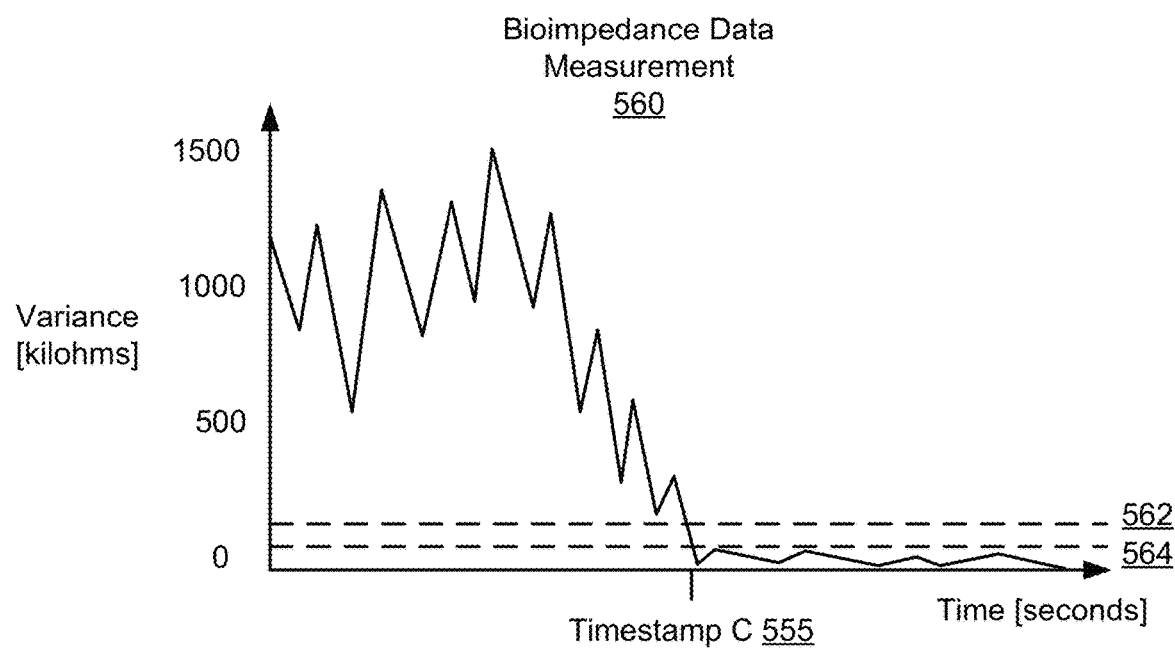
FIG. 5B

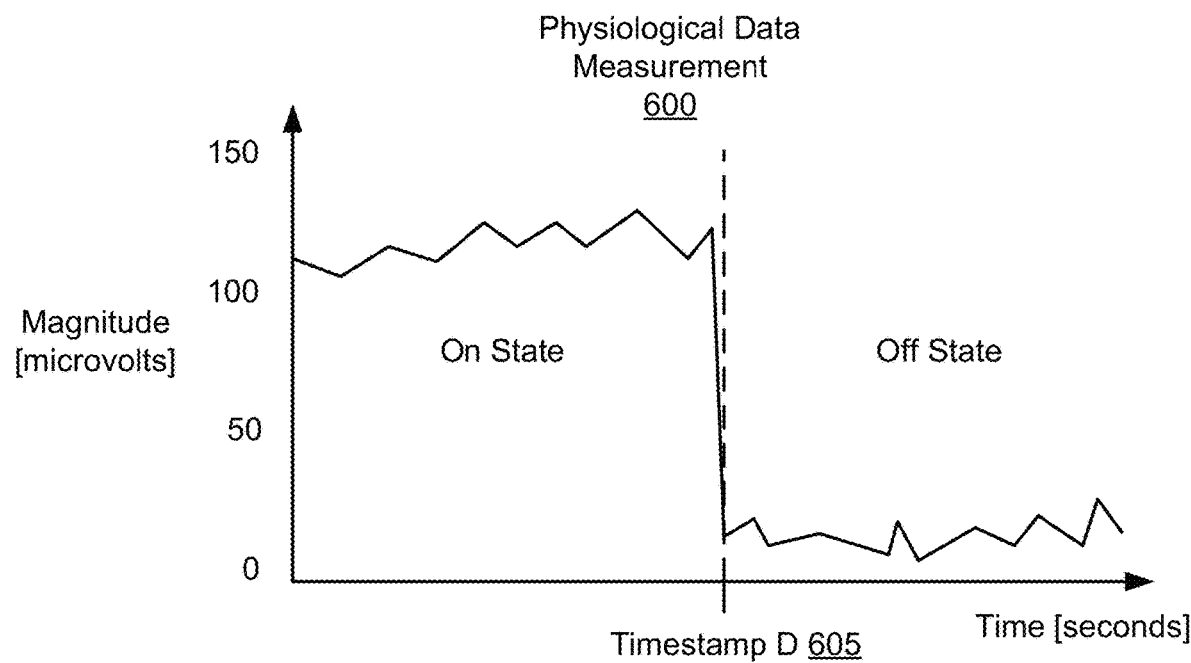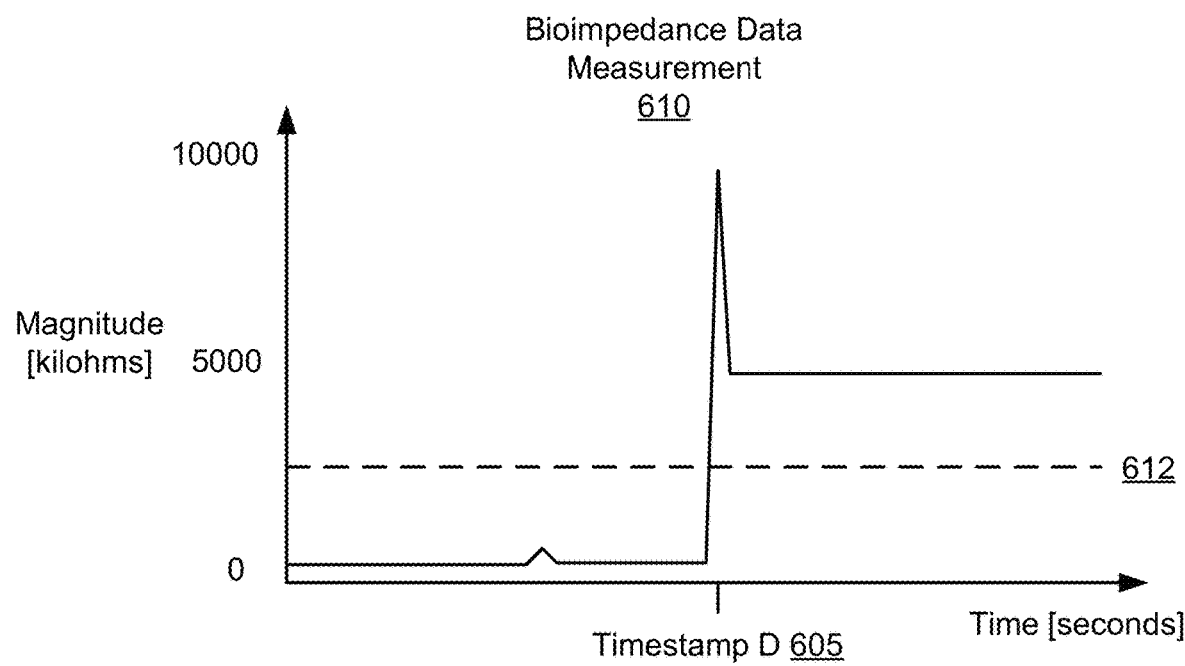
FIG. 6A

700

Receive physiological data from an athletic garment worn by a user while performing an exercise.
710

Receive bioimpedance data from the athletic garment.
720

Determine a magnitude value of a sample of the bioimpedance data.
730

Determine a variance value of the sample of the bioimpedance data.
740

Provide biofeedback in response to the magnitude value being less than a magnitude threshold value and the variance value being less than a variance threshold value.
750

FIG. 7

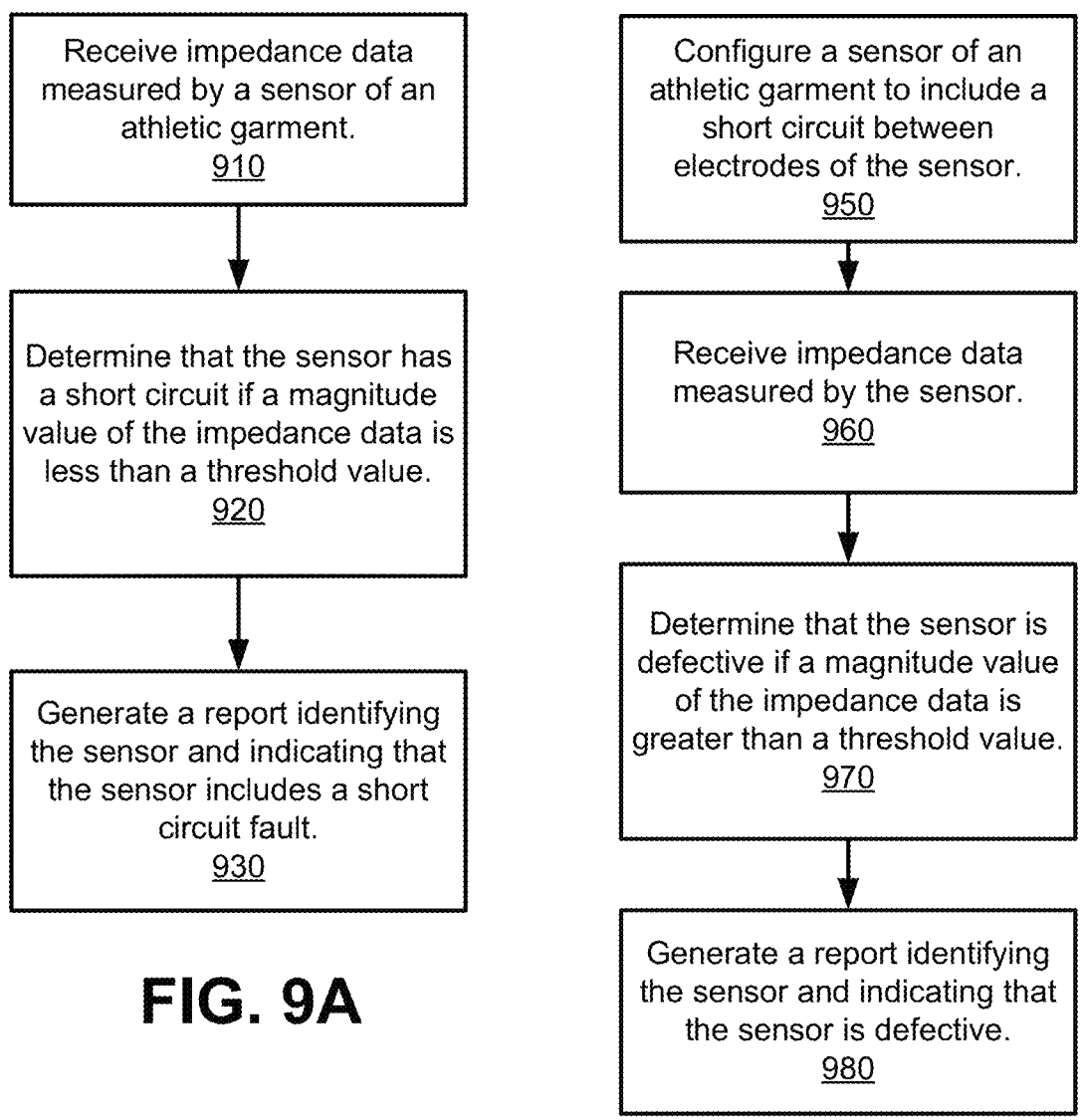

DETERMINING SENSOR DATA QUALITY BASED ON BIOIMPEDANCE INFORMATION

CROSS-REFERENCE TO RELATED APPLICATIONS

This application is a Continuation of co-pending U.S. application Ser. No. 15/257,739 filed on Sep. 6, 2016, which claims the benefit of and priority to U.S. Provisional Application No. 62/218,207 filed Sep. 14, 2015, which is incorporated by reference herein in its entirety.

BACKGROUND

1. Field of Art

This description generally relates to sensor-equipped athletic garments, and specifically to determining sensor data quality based on bioimpedance information.

2. Description of the Related Art

Bioimpedance describes electrical properties of biological tissue. Biological tissues and cells are conductive and can be modeled as resistive or capacitive elements. When current flows through biological tissue of a person, the corresponding bioimpedance can be measured by electrodes contacting the skin of the person. Existing technologies such as bioelectrical impedance analysis use bioimpedance data to estimate body composition information such as a person's percentage of body fat.

Sensors can record a variety of information about the human body. For example, electrocardiograph (ECG) electrodes can measure electrical signals from the skin of a person that are used to determine the person's heart rate. In addition, electromyography (EMG) electrodes can measure electrical activity generated by a person's muscles. Biofeedback such as heart rate and muscle activation information may be useful for evaluating the person's physiological condition, for instance, while exercising. However, the person's body is frequently moving while the person is exercising. Thus, a sensor on the person's body configured to measure heart rate or muscle activation information may shift or lose contact with the skin of the person. Consequently, the data measured by the sensor may have a poor quality or be unreliable. It is desirable and challenging to determine a solution to provide biofeedback based on high quality sensor data measured while a person is exercising.

SUMMARY

An exercise feedback system determines sensor data quality received from a sensor-equipped athletic garment based on bioimpedance information. The athletic garment includes sensors that can generate physiological data and bioimpedance data while an athlete wears the athletic garment while exercising. If the sensors have a stable contact with the skin of the athlete, the sensors generate high quality physiological data. However, if the sensors have unstable or no contact with the skin of the athlete, the sensors generate low quality physiological data as a result of inadequate contact with the athletes' skin. The exercise feedback system uses the magnitude and/or variance of the bioimpedance data to determine whether the physiological data is high or low quality. If the physiological data is high quality, the exercise feedback system can generate and provide reliable feedback based on the physiological data for display to the athlete. For example, the biofeedback indicates which muscles the athlete is heavily using while performing an exercise.

The sensors of the athletic garment can measure impedance data in addition to bioimpedance data. A sensor measure impedance (or "bioimpedance") data representative of the contact the sensor makes with a user's skin. Bioimpedance indicates how well biological tissue or cells impede an electric current flow. In other words, bioimpedance describes the conductivity of a person's body between sensor electrodes. For instance, fat cells have a higher bioimpedance than blood cells. The exercise feedback system determines a magnitude value of a sample of the bioimpedance data. The magnitude value has an upper limit based on a resistor coupled between two electrodes of the sensor. The exercise feedback system also determines a variance value of the sample of the bioimpedance data. The exercise feedback system provides biofeedback in response to the magnitude value being less than a magnitude threshold value and the variance value being less than a variance threshold value. The exercise feedback system provides the biofeedback to a client device for display to the user, and the biofeedback indicates a metric of performance of the exercise based on the physiological data.

In another embodiment, the exercise feedback system performs a quality assurance test for a garment. The exercise feedback system receives impedance data generated by each sensor of the garment. The garment includes a processing unit configured to process the impedance data. Each sensor includes a pair of electrodes coupled to the processing unit by a pair of conductive traces. For each sensor of the garment, the exercise feedback system determines whether a magnitude value of the impedance data generated by the sensor is greater than a threshold value. The exercise feedback system identifies a number of defective sensors based on the determinations for each sensor. The exercise feedback system generates a report indicating a test metric of the garment based on the number of defective sensors.

BRIEF DESCRIPTION OF DRAWINGS

FIG. 5A shows graphs of sensor magnitude data and bioimpedance magnitude data according to one embodiment.

FIG. 5B shows graphs of sensor magnitude data and bioimpedance variance data according to one embodiment.

FIG. 6A shows graphs of sensor magnitude and bioimpedance magnitude according to one embodiment.

FIG. 7 is a flowchart of a process for providing biofeedback based on bioimpedance according to one embodiment.

FIG. 9A is a flowchart of a process for testing for short circuits in a sensor-equipped athletic garment according to one embodiment.

FIG. 9B is a flowchart of a process for testing for defective sensors in a sensor-equipped athletic garment according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. System Overview

Figure 1:
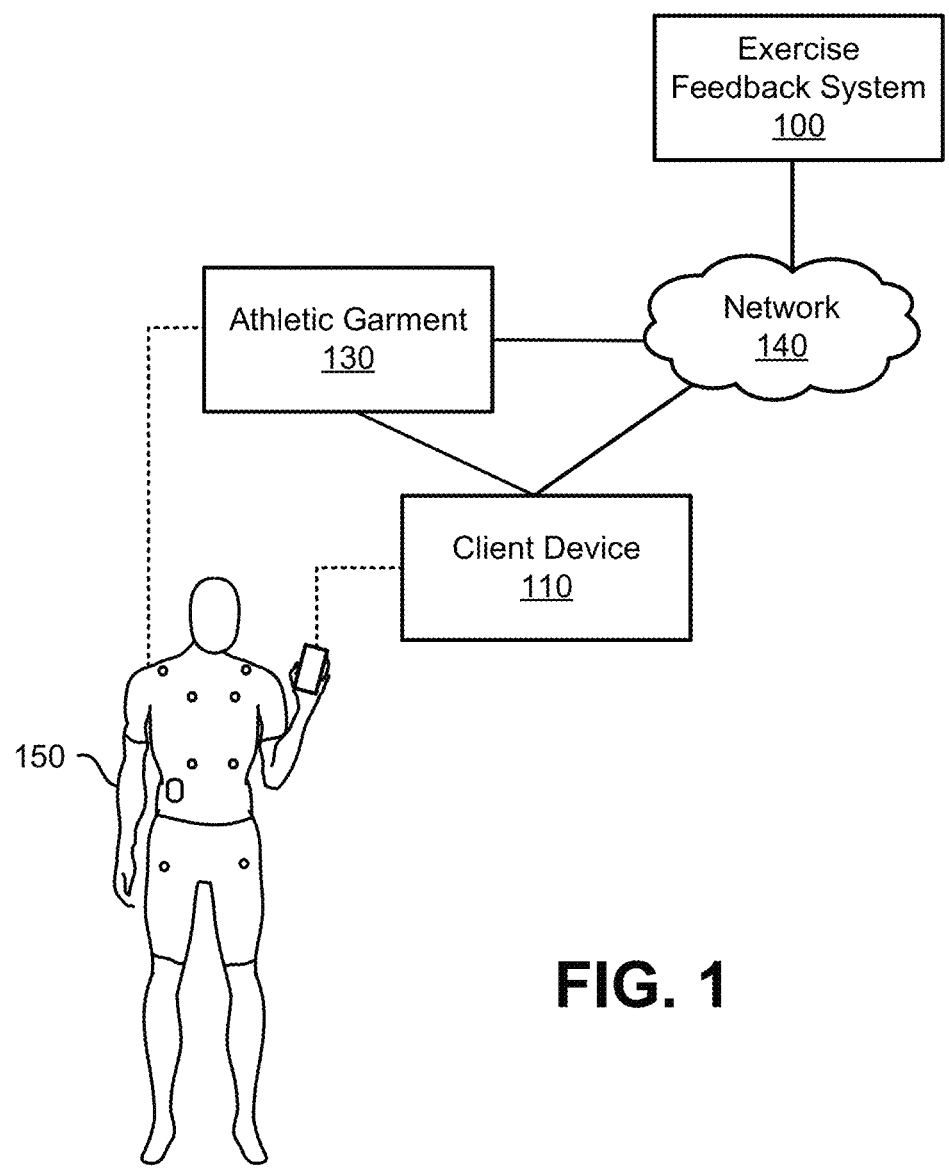
FIG. 1 is a diagram of a system environment for determining sensor data quality according to one embodiment.

Figure (FIG. 1 is a diagram of a system environment for determining sensor data quality according to one embodiment. The system architecture includes an exercise feedback system 100, client device 110, and athletic garment 130 communicatively coupled together via a network 140. Users 150 of the exercise feedback system 100 are also referred to herein as "athletes." In other embodiments, different and/or additional entities can be included in the system architecture.

The client device 110 is a computing device capable of receiving user input as well as transmitting and/or receiving data via the network 140. A client device is a device having computer functionality, such as a smartphone, personal digital assistant (PDA), a mobile telephone, tablet, laptop computer, desktop computer, or another suitable device. In one embodiment, a client device executes an application allowing a user of the client device to interact with the exercise feedback system 100. For example, a client device executes a browser application to enable interaction between the client device and the exercise feedback system 100 via the network 140. In another embodiment, a client device interacts with the exercise feedback system 100 through an application programming interface (API) running on a native operating system of the client device, such as IOS® or ANDROID™.

The network 140 includes any combination of local area and/or wide area networks, including both wired and/or wireless communication systems. In one embodiment, the network 140 uses standard communications technologies and/or protocols. For example, the network 140 includes communication links using technologies such as Ethernet, 802.11, worldwide interoperability for microwave access (WiMAX), 3G, 4G, code division multiple access (CDMA), digital subscriber line (DSL), BLUETOOTH®, Wi-Fi, ZIGBEE®, other suitable close-range networks, etc. Examples of networking protocols used for communicating via the network 140 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 140 may be represented using any suitable format, such as hypertext markup language (HTML) or extensible markup language (XML). In some embodiments, all or some of the communication links of the network 140 may be encrypted using any suitable technique or techniques.

An athlete 150 wears the athletic garment 130 while performing exercises. The athletic garment 130 records physiological data, e.g., muscle activation data or heart rate data, of the athlete, as well as bioimpedance data. The exercise feedback system 100 can determine whether the physiological data is high quality or lower quality data based on bioimpedance data. If the physiological data is high quality data, the exercise feedback system 100 can generate exercise feedback (e.g., biofeedback) customized for the athlete 150. The athlete 150 may view the exercise feedback displayed on a user interface of the client device 110.

II. Athletic Garment

Figure 2:
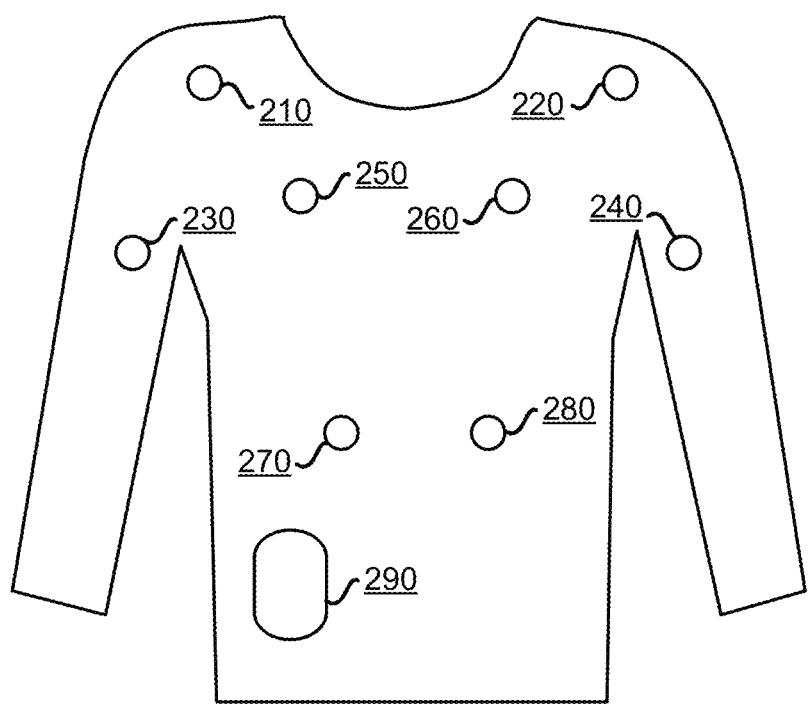
FIG. 2 is a diagram of a sensor-equipped athletic garment according to one embodiment.

FIG. 2 is a diagram of a sensor-equipped athletic garment 130 according to one embodiment. The athletic garment 130 includes sensors that contact the skin of an athlete 150 wearing the athletic garment 130. For example, the sensors can be electrodes that measure electromyography (EMG) signals (electrical signals caused by muscle cells) also referred to as muscle activation data or electrocardiograph (ECG) signals (electrical signals caused by depolarization of the user's heart muscle in particular) also referred to as heart rate data. The sensors may also include other types of sensors such as accelerometers and gyroscopes (which generate motion data based on the athlete's movement), temperature sensors, pressure sensors, humidity sensors, etc. The sensors generate physiological data of the athlete based on the measured signals. The sensors are communicatively coupled to a processing unit 290 (which may be referred to as a "core"). The processing unit 290 can aggregate and analyze the physiological data from the sensors. The processing unit 290 can also provide the physiological data to the client device 110 or exercise feedback system 100 via the network 140.

In the embodiment shown in FIG. 2, the athletic garment 130 includes eight sensors the record muscle activation data from the athlete's muscles nearby each sensor. In particular, sensors 210 and 220 located on the right and left shoulder of the athletic garment 130 can record muscle activation data of the athlete's deltoid muscles. Sensors 230 and 240 located on the right and left sleeves of the athletic garment 130 can record muscle activation data of the athlete's triceps and/or biceps muscles. Sensors 250 and 260 located on the right and left chest of the athletic garment 130 can record muscle activation data of the athlete's pectoral muscles. Sensors 270 and 280 located on the right and left abdomen of the athletic garment 130 can record muscle activation data of the athlete's abdominal and oblique muscles. Though the athletic garment 130 shown in FIG. 2 includes eight sensors and the processing unit 290, in other embodiments, the athletic garment 130 can include any number of sensors or other types of components or electronics at any location or configuration within the athletic garment 130.

It should be noted that while the athletic garment 130 shown in FIG. 2 is a long sleeve shirt, the principles described herein apply equally to any garment, including but not limited to a short sleeved shirt, a tank top, pants, shorts, or any other suitable garment. In embodiments where the athletic garment 130 is a pant, sensors of the athletic garment 130 can record muscle activation data from muscles on an athlete's lower body, e.g., quadriceps, glutes, hamstrings, calves, and the like.

III. Bioimpedance Measurement

Figure 3A:
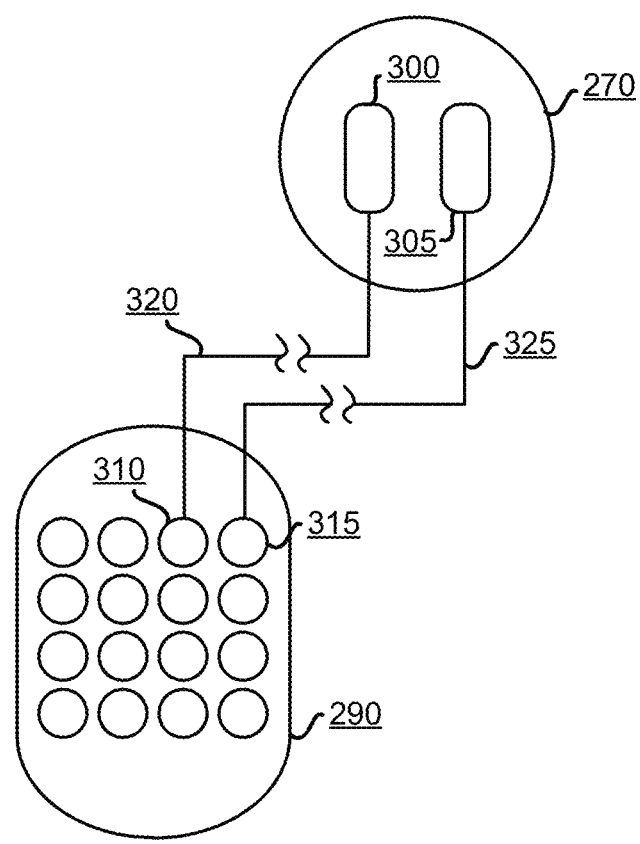
FIG. 3A is a diagram of electrodes of a sensor of the athletic garment shown in FIG. 2 according to one embodiment.

FIG. 3A is a diagram of electrodes of the sensor 270 of the athletic garment 130 shown in FIG. 2 according to one embodiment. The sensor 270 includes a first electrode 300 and a second electrode 305. When an athlete 150 wears the athletic garment 130, the electrodes 300 and 305 contact the skin of the athlete. The processing unit 290 includes multiple conductive elements (e.g., conductive pads) that are coupled to sensors of the athletic garment 130 via conductive traces. For example, the first electrode 300 is coupled to first conductive element 310 via the conductive trace 320. The second electrode 305 is coupled to second conductive element 315 via the conductive trace 325. In some embodiments, the conductive traces are embedded and routed inside the athletic garment 130. For example, the athletic garment 130 includes multiple layers and the conductive traces are in between two other layers, e.g., layers of fabric. The conductive traces may be conductively insulated inside the layers of the athletic garment 130. Each sensor of the athletic garment 130 can be configured similar to the sensor 270. Accordingly, the processing unit 290 can receive data (including physiological data and/or bioimpedance data) measured by electrodes of any of the sensors of the athletic garment 130.

Though the conductive elements of the processing unit 290 shown in FIG. 3A are circular, it should be noted that in other embodiments, the conductive elements may be any other shape such as a rectangle or an oval. Additionally, though the electrodes shown in FIG. 3A are shaped as a rectangle with rounded corners, it should be noted that in other embodiments, the electrodes may be any other shape such as a circle or a polygon without rounded corners.

Figure 3B:
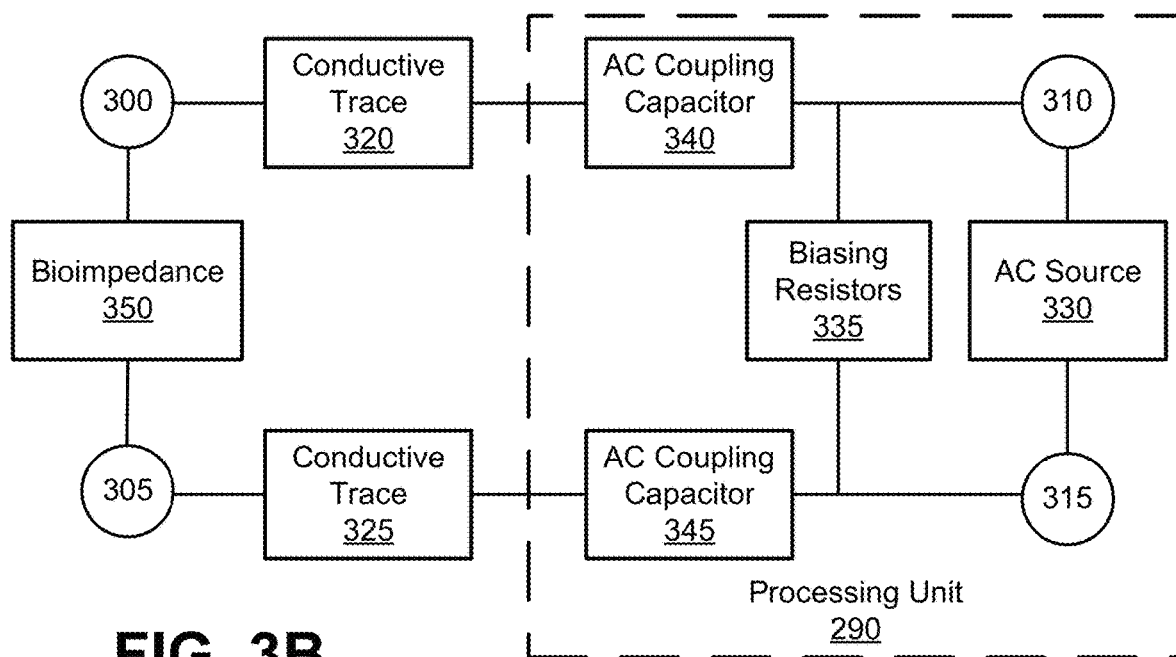
FIG. 3B is a diagram of a circuit of the sensor shown in FIG. 3A with stable contact with an athlete's skin to according to one embodiment.

FIG. 3B is a diagram of a circuit of the sensor 270 shown in FIG. 3A with stable contact with an athlete's skin according to one embodiment. An alternating current (AC) source 330 is coupled in between the first conductive element 310 and the second conductive element 320. Additionally, one or more biasing resistors 335 are coupled in between the first conductive element 310 and the second conductive element 320. An AC coupling capacitor 340 may be coupled in between the first conductive element 310 and the conductive trace 320. Similarly, an AC coupling capacitor 345 may be coupled in between the second conductive element 315 and the conductive trace 325. The AC coupling capacitors 340 and 345 can remove a direct current (DC) common mode offset present in a signal from the circuit that could otherwise saturate a common mode input range of the processing unit 290. In some embodiments, the AC coupling capacitors 340 and 345 in combination with the biasing resistors 335 filter out low frequency noise from the circuit of the sensor 270.

The AC source 330 generates a current that is provided to the first electrode 300 via the conductive trace 320. The first electrode 300 and the second electrode 305 have a stable physical contact with the athlete's skin. Thus, the current travels through the biological tissue of the athlete 150 (wearing the garment 130) from the first electrode 300 and the second electrode 305. The current travels back to the AC source 330 via the conductive trace 325. The peak magnitude of the current is small (e.g., on the scale of nanoamps) so that the athlete will not feel the current from the sensors touching the athlete's skin. In some embodiments, the AC source 330 is at a given frequency that is significantly higher than the highest frequency of interest of the physiological signal, e.g. 250 Hz. A bioimpedance signal captured from the circuit has the same given frequency as the AC source 330. Thus, the sensor 270 or the processing unit 290 can separate the bioimpedance signal from the physiological signal using filtering techniques (e.g., with a low pass filter, high pass filter, or band pass filter implemented in hardware or software). The processing unit 290 measures the voltage across the first conductive element 310 and the second conductive element 320. The bioimpedance 350 of the biological tissue is the measured voltage divided by the current from the AC source 330. Thus, the processing unit 290 (or the exercise feedback system 100) determines the bioimpedance 350 using the measured voltage and the known current.

Figure 3C:
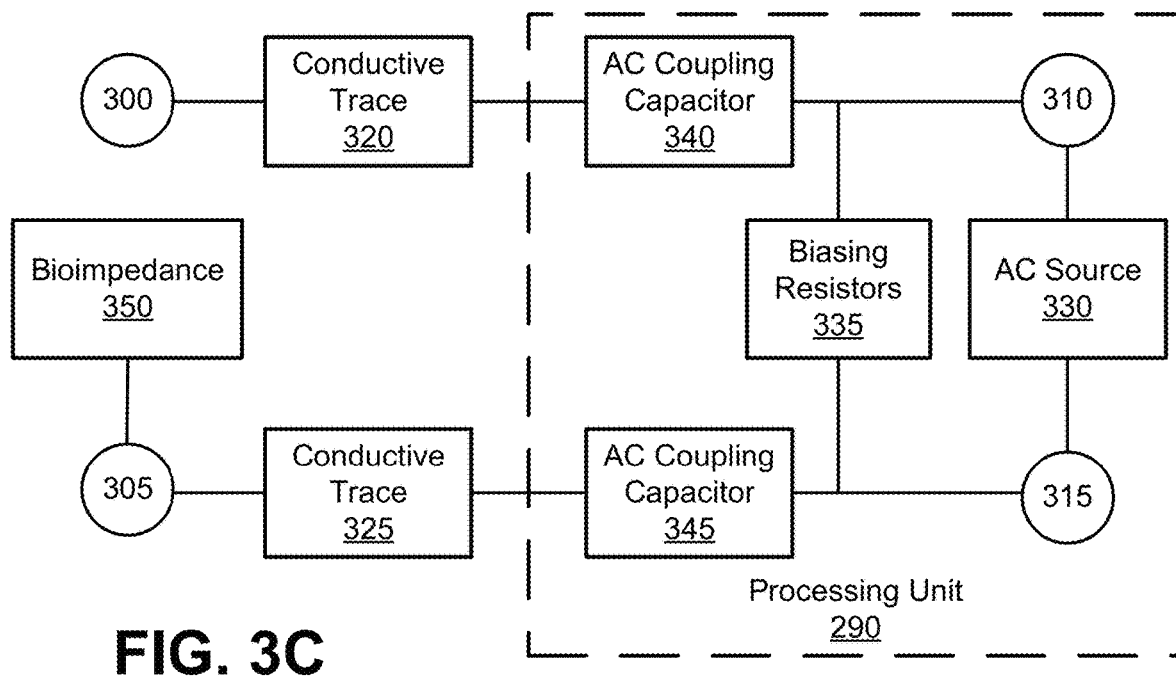
FIG. 3C is a diagram of a circuit of the sensor shown in FIG. 3A with incomplete contact with an athlete's skin to according to one embodiment.

FIG. 3C is a diagram of a circuit of the sensor 270 shown in FIG. 3A with incomplete contact with an athlete's skin to according to one embodiment. The circuit shown in FIG. 3C is substantially the same as the circuit shown in FIG. 3B, except that there is incomplete contact with the skin of the athlete 150. In one embodiment, the first electrode 300 has no physical contact with the athlete's skin, while the second electrode 305 may have stable contact with the athlete's skin. Thus, current from the AC source 330 cannot travel through the biological tissue of the athlete 150 from the first electrode 300 and the second electrode 305. Instead, the current travels across the biasing resistor 335. Thus, the voltage across the first conductive element 310 and the second conductive element 320 measured by the processing unit 290 is based on the resistance of the biasing resistor 335. The resistance of the biasing resistor 335 is significantly larger than the resistance (i.e., bioimpedance) of the athlete's biological tissue, which is usually on the magnitude of tens to hundreds of kilohms (e.g., 200 kilohms).

In one embodiment, the resistance of the biasing resistor 335 is 10 megaohms or greater. Thus, if both electrodes have a stable contact with the athlete's skin, rather than traveling through the biasing resistor 335, the current travels through the biological tissue because it is the path of least resistance. Similarly, if the second electrode 305, or both electrodes, did not have contact with the athlete's skin, the current travels through the biasing resistor 335. The biasing resistor 335 may be advantageous because it provides an upper limit to the determined bioimpedance. Without the biasing resistor 335, the bioimpedance measurement without skin contact may be variable and instable, and the voltage potential of the bioimpedance measurement may saturate the input range of the processing unit 290.

IV. Exercise Feedback System

Figure 4A:
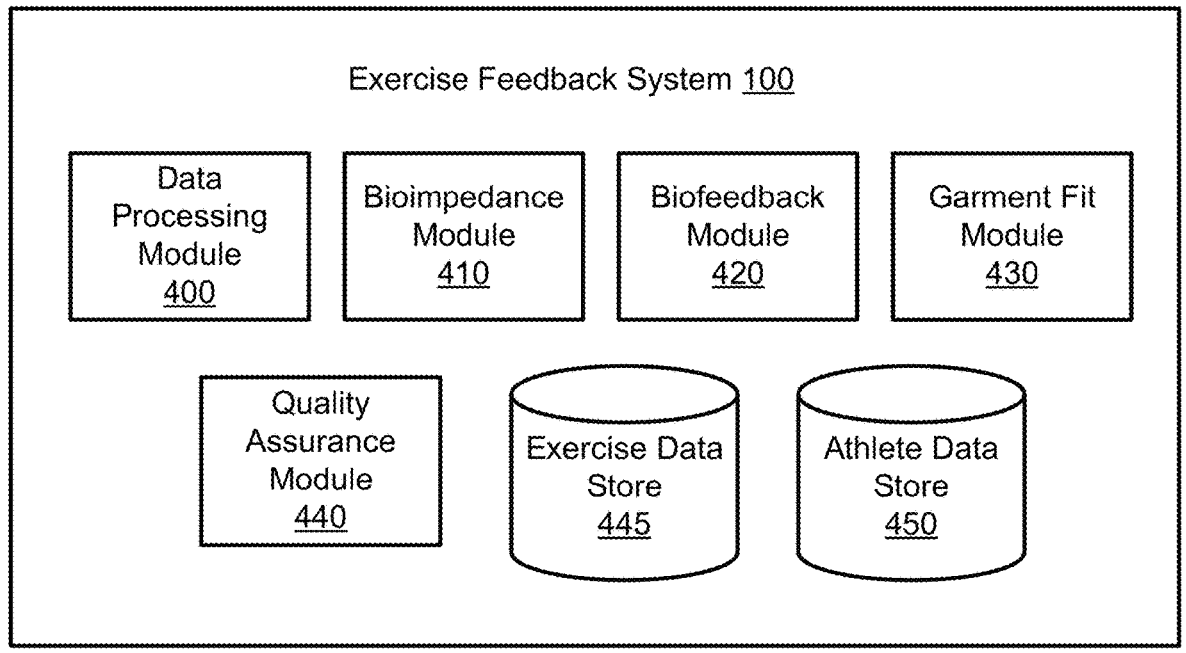
FIG. 4A is a block diagram of an exercise feedback system according to one embodiment.

FIG. 4A is a block diagram of the exercise feedback system 100 according to one embodiment. The exercise feedback system 100 includes a data processing module 400, bioimpedance module 410, biofeedback module 420, garment fit module 430, quality assurance module 440, exercise data store 445, and athlete data store 450. In other embodiments, the exercise feedback system 100 may include additional, fewer, or different components for various applications, which are not shown so as to not obscure the details of the system architecture.

The data processing module 400 processes physiological data generated by sensors of an athletic garment (e.g., athletic garment 130 shown in FIG. 2). The exercise feedback system 100 can receive the physiological data from the client device 110 or the processing unit 290 of the athletic garment 130. The data processing module 400 may process the physiological data by performing noise filtering or feature extraction. Features can include a heart rate or level of muscle activation for a certain muscle of an athlete 150. For example, the data processing module 400 determines the heart rate, e.g., in beats per minute, of an athlete based on the frequency of a sample of sinusoidal heart rate data. In another example, the data processing module 400 determines a level of muscle activation for a particular muscle of an athlete based on the muscle activation data, e.g., a magnitude of the muscle activation data. The level of muscle activation can be represented as "low," "medium," or "high," a percentage value, or another other suitable range of values.

Further, the data processing module 400 can extract temporal patterns from the physiological data. For example, the data processing module 400 determines the time difference between a first muscle activation and a second muscle activation, which may indicate how closely an athlete is performing an exercise with proper form. Additionally, the data processing module 400 determines timestamps of an athlete's movements based on motion data, e.g., a timestamp corresponding to when the athlete started an exercise, ended an exercise, or performed a certain athletic movement such as a jump, sprint, or lift of an arm. The data processing module 400 can store the extracted features in the athlete data store 450 along with information identifying the corresponding athlete.

The data processing module 400 can determine features based on a computation of one or more other features or physiological data. For example, the data processing module 400 computes a ratio of a first level of muscle activation (of an athlete's left biceps muscle) to a second level of muscle activation (of an athlete's right biceps muscle), which can indicate the athlete's balance, form, or other types of metrics. As another example, the data processing module 400 computes a level of fatigue based on an athlete's heart rate and aggregate level of muscle activation across the body.

The bioimpedance module 410 processes bioimpedance and impedance data generated by sensors of an athletic garment (e.g., athletic garment 130 shown in FIG. 2). The exercise feedback system 100 can receive the bioimpedance data from the client device 110 or the processing unit 290 of the athletic garment 130. The bioimpedance module 410 may process the bioimpedance data by performing noise filtering or feature extraction. Based on the bioimpedance data, the bioimpedance module 410 determines a level of contact of a sensor with the skin of an athlete 150 wearing the athletic garment 130. For example, if the average magnitude and variance of the bioimpedance data over a certain time period are each lower than threshold values, the bioimpedance module 410 determines that the sensor has a satisfactory level of contact with the skin. The bioimpedance module 410 may also determine whether or not the athlete is wearing the athletic garment 130, or whether the athletic garment 130 is a proper size fit for the athlete. The bioimpedance module 410 is further described below.

The biofeedback module 420 generates biofeedback for users of the exercise feedback system 100 based on features extracted by the data processing module 400. The biofeedback indicates a metric of performance of an athlete 150 performing exercises. The biofeedback module 420 can store the biofeedback in the athlete data store 450 along with information identifying the corresponding athlete. The biofeedback module 420 can compare the extracted features with features based on reference exercise data from the exercise data store 445. In one example, the reference exercise data indicates a target range of heart rate (e.g., heart rate after exercising or heart rate while performing high intensity exercises) based on demographic information of an athlete (e.g., age or gender). The reference exercise data may be based on exercise data previously collected by the exercise feedback system 100 from a population of users. If the an athlete's heart rate indicated by the extracted features falls within the corresponding target range, then the biofeedback module 420 generates biofeedback indicating that the athlete has a satisfactory heart rate.

In some embodiments, the biofeedback module 420 generates biofeedback based on bioimpedance data. For example, the bioimpedance module 410 determines that the bioimpedance measured by a sensor of the athletic garment 130 worn by an athlete 150 gradually decreases over time. The bioimpedance of dry skin is greater than the bioimpedance of wet skin. Thus, the biofeedback module 420 determines that the athlete is warming-up for exercising based on the decrease in bioimpedance. In particular, since the athlete starts to sweat while warming-up, the athlete's skin gradually becomes wetter (e.g., more damp) and thus conductive. Accordingly, the bioimpedance of the athlete becomes more resistive in nature, in comparison to the capacitive nature of the bioimpedance when the skin is drier. The biofeedback module 420 may compare the bioimpedance data with reference data from the exercise data store 445 indicating an expected improvement (e.g., decrease over time) of bioimpedance data for an athlete that has warmed-up, e.g., based on previously measured bioimpedance data. If the bioimpedance data closely matches the reference data, the biofeedback module 420 determines that the athlete 150 has sufficiently warmed-up for exercising.

The biofeedback module 420 provides biofeedback to the client device 110 for display to an athlete 150. In some embodiments, the biofeedback module 420 provides the biofeedback for display if the bioimpedance module 410 determines that, for one or more sensors of the garment, the sensors are in a satisfactory level of contact with the skin of the athlete 150. If the bioimpedance module 410 determines that one or more sensors are in an unsatisfactory level of contact with the skin of the athlete 150, then the biofeedback module 420 does not provide the biofeedback for display because the physiological data generated by the sensors (and processed by the data processing module 400) may not be reliable or accurate. As an example, low quality physiological data contains undesirable artifacts such as high magnitude peaks or ambient noise if the sensor does not have stable contact with the skin. Thus, biofeedback generated by the biofeedback module 420 using the low quality physiological data may indicate an incorrect muscle activation level of the athlete that is greater than the athlete's actual muscle activation level. The biofeedback module 420 does not provide the incorrect muscle activation level for display to prevent confusing the athlete 150.

In one embodiment, the biofeedback module 420 provides biofeedback as a depiction of muscles overlaid on an image of the athlete 150. For example, the depiction shows the athlete's left and right quadriceps, biceps, triceps, and pectoral muscles. The depiction of each muscle depends on the muscle activation level of the particular muscle. For instance, if the athlete is heavily using the quadriceps muscles while performing a squat exercise, then the biofeedback module 420 shows a depiction indicating that the quadriceps muscles have a high muscle activation level, e.g., by depicting the quadriceps muscles as a larger size compared to other muscle depictions, or in a different color. If the level of contact of a sensor is unsatisfactory, the biofeedback module 420 may hide the depiction of the corresponding muscle.

As an example, the sensors configured to measure physiological data from the athlete's biceps muscles become loose while the athlete 150 is exercising, e.g., because the athlete 150 rolls up sleeves of the athletic garment 130 worn by the athlete 150. The sensors no longer have a stable contact with the athlete's biceps muscles. Thus, the biofeedback module 420 hides the depiction of the biceps muscles, or provides another indication that the physiological data is unavailable or unreliable, e.g., by showing the depiction of the biceps muscles in a darker color or displaying a notification or error message. For instance, a notification informs the athlete 150 to check that the athlete is properly wearing the athletic garment 130.

The biofeedback module 420 may provide other types of notifications and error messages. The biofeedback module 420 can provide an error message indicating that the processing unit 290 on the athletic garment 130 is defective if the bioimpedance module 410 determines that none of the sensors of the athletic garment has a satisfactory level of contact with the athlete's skin. The error message may also inform the user to replace the processing unit 290 with a new processing unit. As another example, the biofeedback module 420 provides a notification informing the user that the sensors do not detect the athlete's body and/or that the athlete 150 should wear the athletic garment 130 before starting or continuing an exercise.

In one embodiment, the biofeedback module 420 generates a notification indicating that biofeedback cannot be provided due to lack sensor contact with the skin of the athlete 150. For example, the biofeedback module 420 determines that the athlete 150 may be wearing another garment underneath the athletic garment 130. Thus, the biofeedback module 420 may disable certain types of biofeedback such as heart rate data that requires that the sensors have contact with the athlete's skin.

In some embodiments, the garment fit module 430 generates requests for exchanges for athletic garments based on bioimpedance data. In particular, the garment fit module 430 may generate a request for an exchange if the bioimpedance module 410 determines that an athletic garment 130 is not a proper size fit for an athlete 150 wearing the athletic garment. In one example, the bioimpedance module 410 determines the athletic garment 130 is too large in size for the athlete 150 because the sensors have an unsatisfactory level of contact with the athlete's skin. In particular, the bioimpedance module 410 may determine that the number of sensors with an unsatisfactory level of contact is greater than an acceptable threshold value. Alternatively, the bioimpedance module 410 may determine that the percentage of sensors of the athletic garment with a satisfactory level of contact is less than an acceptable threshold value. The garment fit module 430 is further described below.

In some embodiments, the quality assurance module 440 determines a quality of the sensors of an athletic garment 130. As an example use case, the quality assurance module 440 conducts quality assurance tests to determine whether an athletic garment 130 has any defective sensors or short circuits during the manufacturing process of the athletic garment 130. The quality assurance module 440 may generate a report including results of the conducted tests, e.g., indicating whether or not the athletic garment 130 passed the tests. The quality assurance module 440 is further described with reference to FIGS. 9A-B in Section VIII. Garment Quality Assurance.

Figure 4B:
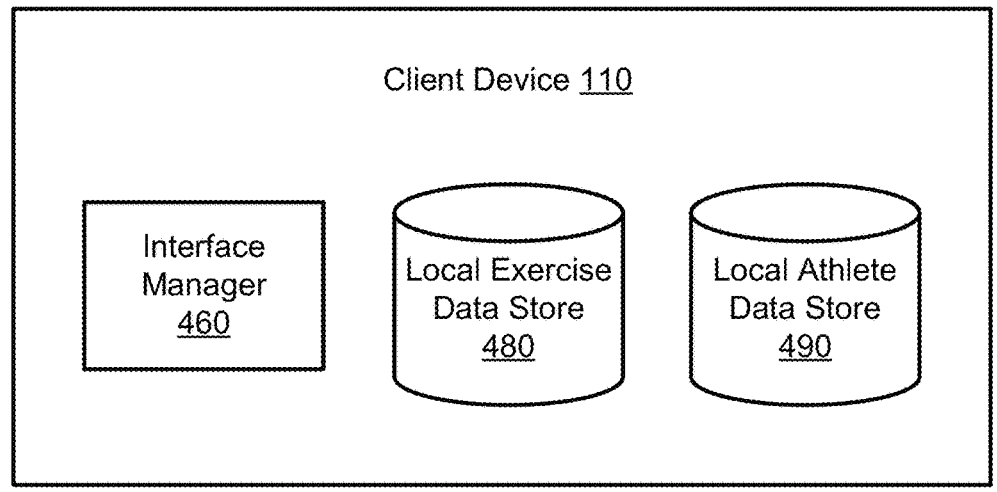
FIG. 4B is a block diagram of a client device according to one embodiment.

FIG. 4B is a block diagram of the client device 110 according to one embodiment. The client device 110 includes an interface manager 460, local exercise data store 480, and local athlete data store 490. In other embodiments, the client device 110 may include additional, fewer, or different components for various applications, which are not shown so as to not obscure the details of the system architecture.

In some embodiments, some or all of the functionality of the exercise feedback system 100 may be performed by or implemented within the client device 110. For example, the client device 110 may include a local biofeedback module to generate biofeedback based on physiological data received from the athletic garment 130 or stored in the local exercise data store 480 or the local athlete data store 490. This can be advantageous because the client device 110 may not always have a network connection while an athlete 150 is exercising (e.g., the athlete's gym does not have internet available). Thus, the biofeedback is generated locally on the client device 110 without having to upload the physiological data to the exercise feedback system 100 for processing. Similarly, the client device 110 may include a local bioimpedance module to determine a level of contact of sensors of the athletic garment 130 with the skin of the athlete 150. Thus, the local biofeedback module can determine whether or not to display biofeedback to the athlete 150 based on the level of contact determined by the local bioimpedance module without requiring a network connection.

The interface manager 460 receives physiological data from the athletic garment 130 and may provide the physiological data to the exercise feedback system 100 for further processing. The interface manager 460 receives biofeedback or other information from the exercise feedback system 100, e.g., reference exercise data or extracted features from the data processing module 400. Based on the received information, the interface manager 460 can generate graphical user interfaces depicting the biofeedback for display to the athlete 150. The interface manager 460 may store physiological data, biofeedback, or other information in the local athlete data store 490. The interface manager 460 may store the reference exercise data and extracted features in the local exercise data store 480.

The interface manager 460 can receive athlete information input by the athlete 150 via the client device 110. The interface manager 460 can store the athlete information in the local athlete data store 490 or provide the athlete information to the exercise feedback system 100 to be stored in the athlete data store 450. The athlete information may describe, e.g., a goal of the athlete, demographic data (age or gender), geographical location, one or more sports that the athlete plays, history of injuries of the athlete, other types of data such as the athlete's weight, height, arm span, waist measurement, clothing size, or shoe size.

V. Sensor Data Quality

FIG. 5A shows graphs of sensor magnitude data and bioimpedance magnitude data according to one embodiment. The graph 500 shows the magnitude (in microvolts) of a sample of physiological data generated by a sensor of the athletic garment 130 over time. For example, the sample of physiological data represents the muscle activation level of a particular muscle of an athlete 150 wearing the athletic garment 130. Peaks in magnitude of the muscle activation level, for example, peak 515, indicate that the athlete 150 exerted more effort using the particular muscle at the time of the peak. For instance, if the particular muscle is the biceps muscle of the athlete, then the peaks may correspond to each repetition of an upper body exercise that the athlete 150 is performing (e.g., curls, pull-ups, or overhead press exercises). The sample of physiological data may also include artifacts such as peaks in magnitude that do not correspond to instances of increased muscle activation level. For example, the artifact 520 is a peak occurring at timestamp A 505. The artifact 520 may have been generated by the sensor because the sensor's contact with the athlete's skin momentarily became unstable (e.g., no steady physical contact), for example, due to the sensor being hit by an object or the athlete 150 shifting the athletic garment 130 on the athlete's body. The sensor may also measure artifacts due to other factors such as ambient noise and motion, friction, or rubbing of the athletic garment 130.

The graph 530 shows the magnitude (in kilohms) of a sample of bioimpedance data generated by the sensor of the athletic garment 130 over time. The time axis is equivalent between graph 500 and graph 530. Thus, the peak 540 in magnitude at timestamp B 535 occurs just prior to the artifact 520 at timestamp 505. Similar to the artifact 520, the magnitude of the bioimpedance data increased when the sensor's contact with the athlete's skin momentarily became unstable. If the magnitude of the peak 540 is greater than an upper magnitude threshold 542, e.g., 1000 kilohms, the bioimpedance module 410 determines that the sample of physiological data has low quality. In other words, magnitude values greater than the upper magnitude threshold 542 indicate that the sensor does not have adequate contact with the athlete's skin. Thus, physiological data generated by the sensor may likely be unreliable or inaccurate. In contrast, if the magnitude of the peak 540 is less than a lower magnitude threshold 544, e.g., 800 kilohms, the bioimpedance module 410 determines that the sample of physiological data has high quality. In other words, magnitude values less than the lower magnitude threshold 544 indicate that the sensor has adequate contact with the athlete's skin. Thus, physiological data generated by the sensor is likely reliable and accurate. The upper and lower magnitude thresholds may be adjustable, e.g., based on a calibration process to tune the thresholds, which may differ between athletic garments due to variations in sensor hardware.

In response to a low quality determination of the bioimpedance module 410, the biofeedback module 420 may discard data generated by the sensor until the bioimpedance module 410 determines a high quality sample of physiological data. Thus, the biofeedback module 420 will avoid using artifacts such as artifact 520 to generate biofeedback. This is advantageous because the biofeedback module 420 will avoid generating inaccurate biofeedback and displaying the inaccurate biofeedback to the athlete 150. For instance, the biofeedback module 420 does not erroneously indicate that the athlete 150 heavily exerted the athlete's biceps muscles while the athlete's arms were actually stationary.

In the graph 500, the artifact 520 has a magnitude of 150 microvolts, which is significantly greater than the magnitude of the peak 515 (50 microvolts). However, in some embodiments, the magnitude of artifacts may be closer to the magnitude of the correct peaks. Thus, by using the magnitude of the bioimpedance data, the bioimpedance module 410 can discard artifacts that would not be identifiable based only on the magnitude of the sample of physiological data. In particular, the magnitude of the bioimpedance data may be greater than the upper magnitude threshold even though the magnitude of a corresponding artifact is not significantly greater than the average magnitude of peaks in the sample of physiological data.

FIG. 5B shows graphs of sensor magnitude data and bioimpedance variance data according to one embodiment. The graph 550 shows the magnitude (in microvolts) of a sample of magnitude data generated by a sensor of the athletic garment 130 over time. For example, the sample of physiological data represents the muscle activation level of a particular muscle of an athlete 150 wearing the athletic garment 130. The sample is in a low quality data state before timestamp C 555, e.g., because the average magnitude is less than an expected average magnitude limit. For instance, the biofeedback module 420 expects an average magnitude greater than 200 microvolts. On the other hand, the sample is in a high quality data state after timestamp C 555, e.g., because the average magnitude is greater than the expected average magnitude limit and the magnitude has a smaller level of variance compared to that of the lower quality data state.

The graph 560 shows the variance (in kilohms) of a sample of bioimpedance data generated by the sensor of the athletic garment 130 over time. The time axis is equivalent between graph 550 and graph 560. If the variance is less than a lower variance threshold 564, e.g., 50 kilohms, the bioimpedance module 410 determines that the sample of physiological data is in a high quality data state. In contrast, if the variance is greater than an upper variance threshold 562, e.g., 100 kilohms, the bioimpedance module 410 determines that the sample of physiological data is in a low quality data state. Similar to the magnitude thresholds, the variance thresholds may also be adjustable.

Figure 5C:
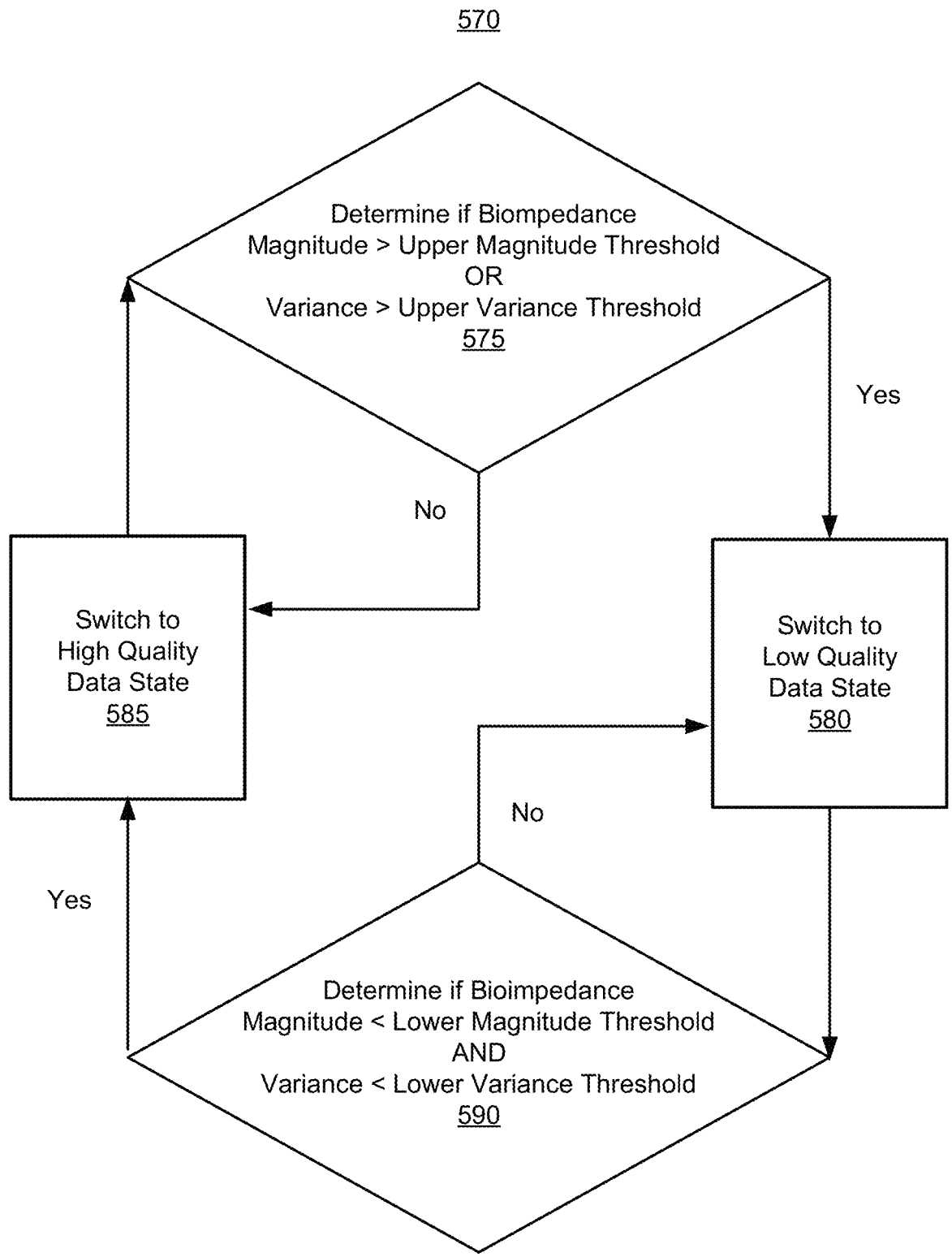
FIG. 5C is a flowchart of a process for determining a data state according to one embodiment.

FIG. 5C is a flowchart of a process 570 for determining a data state according to one embodiment. The bioimpedance module 410 uses the process 570, which is based on the thresholds shown in FIGS. 5A-B, to determine whether a sample of physiological data generated by a sensor of the athletic garment 130 is in a high or low quality data state. The process 570 may include different or additional steps than those described in conjunction with FIG. 5C in some embodiments or perform steps in different orders than the order described in conjunction with FIG. 5C.

The bioimpedance module 410 determines 575 if the magnitude of the bioimpedance corresponding to the sample of physiological data is greater than the upper magnitude threshold or if the variance of the bioimpedance is greater than the upper variance threshold. If so, the bioimpedance module 410 switches 580 the sample of physiological data to a low quality data state. If not, the bioimpedance module 410 switches 585 the sample of physiological data to a high quality data state. From the low quality data state, the bioimpedance module 410 determines 590 if the magnitude of the bioimpedance is lower than the lower magnitude threshold and if the variance of the bioimpedance is lower than the lower variance threshold. If so, the bioimpedance module 410 switches 585 the sample of physiological data to the high quality data state. If not, the bioimpedance module 410 switches 580 the sample of physiological data to the low quality data state.

FIG. 6A shows graphs of sensor magnitude and bioimpedance magnitude according to one embodiment. The graph 600 shows the magnitude (in microvolts) of a sample of physiological data generated by a sensor of the athletic garment 130 over time. For example, the sample of physiological data represents the muscle activation level of a particular muscle of an athlete 150 wearing the athletic garment 130. The athletic garment 130 is in an "on state" before timestamp D 605 because an athlete is wearing the athletic garment 130. The athletic garment 130 is in an "off state" after timestamp D 605 because the athlete is not wearing the athletic garment 130.

The graph 610 shows the magnitude (in kilohms) of a sample of bioimpedance data generated by the sensor of the athletic garment 130 over time. The time axis is equivalent between graph 600 and graph 610. If the magnitude is less than an "on state" threshold 612, e.g., 2500 kilohms, the bioimpedance module 410 determines that the athletic garment 130 is in the "on state." In contrast, if the magnitude is greater than the "on state" threshold 612, the bioimpedance module 410 determines that athletic garment 130 is in the "off state." Similar to the magnitude and variance thresholds, the "on state" threshold may also be adjustable, e.g., based on the value of the biasing resistors 335 of the processing unit 290 (previously shown in FIGS. 3B-C).

In one embodiment, the magnitude of the bioimpedance has a sharp peak in the transition from the "on state" to the "off state." The magnitude of the bioimpedance settles to an "off state" magnitude that depends on the value of the biasing resistors 335. In other embodiments, the magnitude of the bioimpedance does not have a peak in the transition, but rather increases more gradually from the "on state" to the "off state." For instance, the processing unit 290 includes capacitors to dampen the change in magnitude.

Figure 6B:
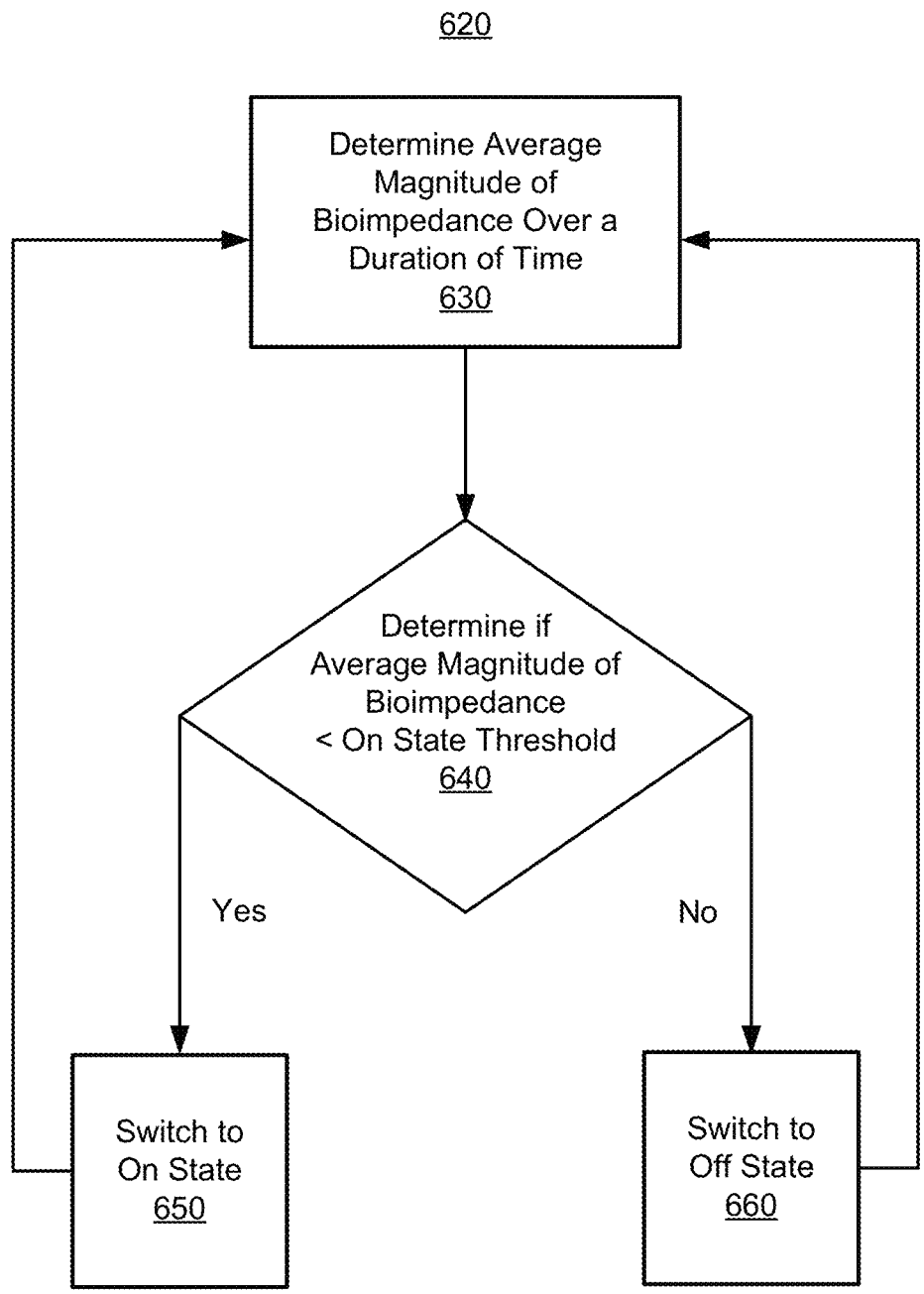
FIG. 6B is a flowchart of a process for determining a state of an athletic garment according to one embodiment.

FIG. 6B is a flowchart of a process 620 for determining a state of an athletic garment 130 according to one embodiment. The bioimpedance module 410 uses the process 620, which is based on the threshold shown in FIG. 6A, to determine whether the athletic garment 130 is in an "on state" or "off state." The process 620 may include different or additional steps than those described in conjunction with FIG. 6B in some embodiments or perform steps in different orders than the order described in conjunction with FIG. 6B.

The bioimpedance module 410 determines 630 an average magnitude of bioimpedance over a duration of time (e.g., a certain number of milliseconds or seconds such as 5 seconds, or certain number of data points) of a sample of data. The bioimpedance module 410 determines 640 if the average magnitude of bioimpedance is less than the "on state" threshold. If so, the bioimpedance module 410 switches 650 (or maintains) the state of the athletic garment 130 to the "on state." If not, the bioimpedance module 410 switches 660 (or maintains) the state of the athletic garment 130 to the "off state." In some embodiments, the bioimpedance module 410 switches the state of the athletic garment 130 based on the bioimpedance of multiple sensors. For example, the bioimpedance module 410 switches to the "on state" if the average magnitude of bioimpedance is less than the "on state" threshold for a threshold number of sensors (e.g., six out of eight sensors of the athletic garment 130).

In some embodiments, the exercise feedback system 100 pauses an exercise workout that the athlete 150 is performing if the bioimpedance module 410 switches the state of the athletic garment 130 to the "off state." In an example use case, an exercise workout includes a sequence of timed exercises such as pull-ups, push-ups, and sit-ups, for instance displayed by the client device 110 of the user in sequence. The exercise feedback system 100 automatically progresses from one exercise to another once the time allocated for an exercise has elapsed (e.g., one minute of pull-ups followed by one minute of push-ups) or once the exercise feedback system determines (for instance, based on physiological data received from the athletic garment) that the athlete has completed the current exercise. Thus, the exercise feedback system 100 can provide feedback to the athlete displaying a current exercise in the exercise workout sequence and indicating whether the athlete is keeping up with the pace of the exercise workout. If the exercise feedback system 100 pauses the exercise workout, the exercise feedback system 100 will not automatically progresses from one exercise to another, but instead wait for the exercise feedback system 100 resumes or ends the exercise workout. Thus, the athlete can take a break to readjust the athletic garment 130 or rest before continuing the exercise workout.

Following in the same example use case, the exercise feedback system 100 resumes the exercise workout if the bioimpedance module 410 switches the state of the athletic garment 130 to the "on state" within a timeout period (e.g., 20 minutes or an adjustable timeout period). Otherwise, the exercise feedback system 100 ends the exercise workout. The interface manager 460 may provide notifications (e.g., visual, audio, or tactile) to the client device 110 to inform the athlete that the exercise workout has been paused, resumed, or ended. In one embodiment, the exercise feedback system 100 does not begin an exercise workout until the bioimpedance module 410 determines that the athletic garment 130 is in the "on state."

VI. Providing Biofeedback

FIG. 7 is a flowchart of a process 700 for providing biofeedback based on bioimpedance according to one embodiment. In some embodiments, the process 700 is performed by the exercise feedback system 100—e.g., modules of the exercise feedback system 100 described with reference to FIG. 4A—within the system environment in FIG. 1. The process 700 may include different or additional steps than those described in conjunction with FIG. 7 in some embodiments or perform steps in different orders than the order described in conjunction with FIG. 7.

The data processing module 400 receives 710 physiological data from an athletic garment 130 worn by a user (e.g., the athlete 150) while performing an exercise. The athletic garment 130 includes sensors configured to generate the physiological data and bioimpedance data. The physiological data may describe muscle activation of the user's muscles or the user's heart rate while performing an exercise. The bioimpedance module 410 receives 720 bioimpedance data from the athletic garment 130. The bioimpedance data is based on a level of physical contact between one of the sensors and a portion of skin of the user. For example, the sensor is contacting the skin on the user's quadriceps muscles, and the level of physical contact may be "stable", "unstable", or "no contact". The bioimpedance module 410 determines 730 a magnitude value (or, more generally, a first "parameter value") of a sample of the bioimpedance data. The magnitude value may have an upper limit based on a resistor (e.g., the biasing resistors 335) coupled to the sensors. The bioimpedance module 410 determines 740 a variance value (or, more generally, a second "parameter value") of the sample of the bioimpedance data.

The biofeedback module 420 provides 750 biofeedback in response to the magnitude value being less than a magnitude threshold value and the variance value being less than a variance threshold value. In some embodiments, the biofeedback module 420 provides biofeedback in response to the magnitude value or the variance value being outside of a predetermined range. The biofeedback module 420 can provide the biofeedback to a client device 110 for display to the user, e.g., while the user is exercising or after the user finishes exercising. The biofeedback may indicate a metric of performance of the exercise based on the physiological data. For example, if the data processing module 400 determines that the muscle activation level of the user's right biceps is greater than of the user's left biceps based on the physiological data, the biofeedback indicates that the user is not performing the exercise with proper balance. Additionally, the biofeedback may inform the user about certain exercises that can help the user practice improving the user's balance.

VII. Exchanging Athletic Garments

Figure 8:
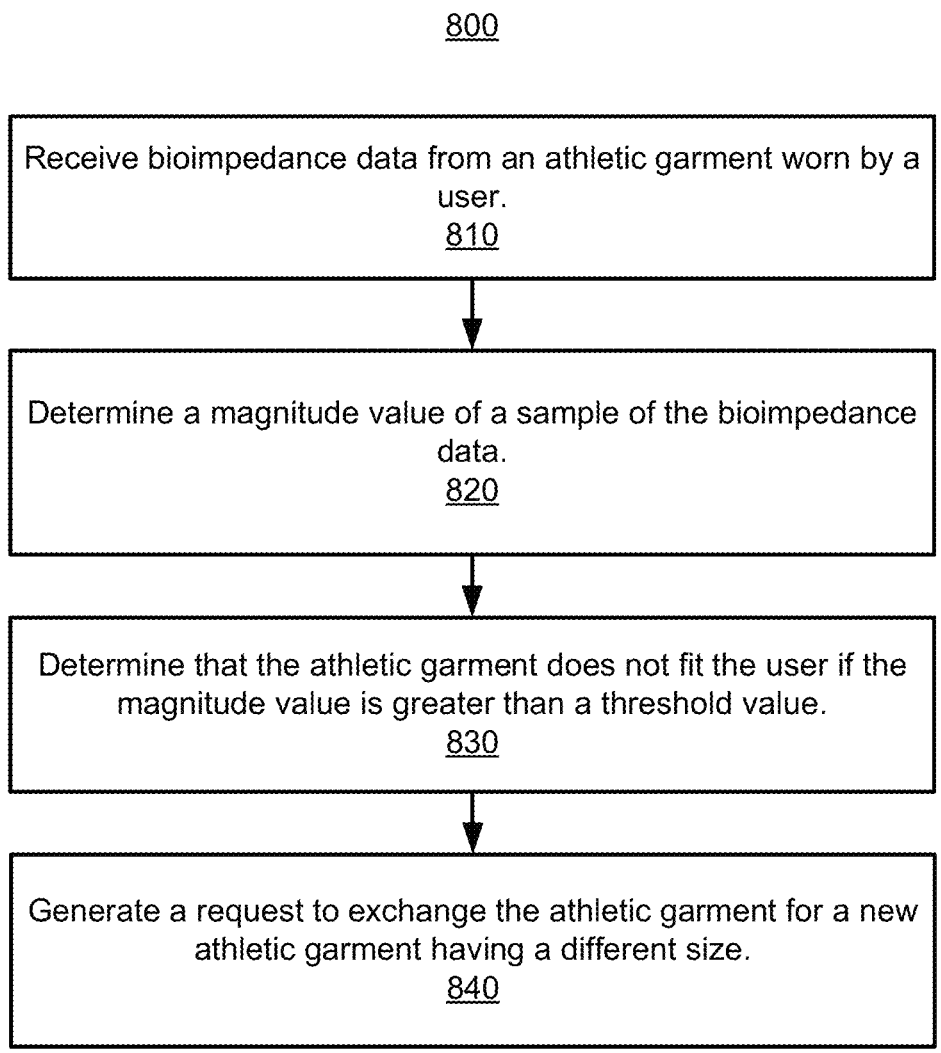
FIG. 8 is a flowchart of a process for generating a request to exchange an athletic garment according to one embodiment.

FIG. 8 is a flowchart of a process 800 for generating a request to exchange an athletic garment according to one embodiment. In some embodiments, the process 800 is performed by the exercise feedback system 100—e.g., modules of the exercise feedback system 100 described with reference to FIG. 4A—within the system environment in FIG. 1. The process 800 may include different or additional steps than those described in conjunction with FIG. 8 in some embodiments or perform steps in different orders than the order described in conjunction with FIG. 8.

The bioimpedance module 410 receives 810 bioimpedance data from an athletic garment 130 worn by a user (e.g., an athlete 150). The bioimpedance data is based on a level of physical contact between sensors of the athletic garment 130 and a portion of skin of the user. The bioimpedance module 410 determines 820 a magnitude value of a sample of the bioimpedance data. The garment fit module 430 determines 830 that the athletic garment 130 does not fit the user if the magnitude value is greater than a threshold value. In one embodiment, the bioimpedance module 410 may determine a number of sensors with an unsatisfactory level of contact with the skin of the user (e.g., the magnitude value for each sensor is greater than the threshold value), for example, due to the magnitude and/or variance of the bioimpedance data being too high. Loosely fitted athletic garment 130 may likely result in some of the sensors having an unstable or no physical contact with the skin of the user. Thus, if the number of sensors with an unsatisfactory level of contact is greater than a threshold value (e.g., two), the bioimpedance module 410 determines that the athletic garment 130 is too large in size for the user.

The garment fit module 430 can receive user information about the user in response to determining that the athletic garment 130 does not fit the user. The user information may indicate the garment size (e.g., small, medium, large, or extra-large), height, gender, mailing or billing address, contact information (e.g., phone number or email address), or other information about the user. The garment fit module 430 generates 840 a request to exchange the athletic garment for a new athletic garment having a different size. For example, the garment fit module 430 generates the request for a new athletic garment having the user's garment size indicated by the received user information. Further, the garment fit module 430 may generate the request to have the new athletic garment mailed to the address of the user. The garment fit module 430 can provide a notification indicating the request to exchange to a client device 110 for display to the user, e.g., in a user interface generated by the interface manager 460. Additionally, the garment fit module 430 may provide the notification via email or phone using the user's contact information.

VIII. Garment Quality Assurance

In some embodiments, the exercise feedback system 100 uses impedance data generated by sensors of the athletic garment 130 for quality assurance tests during a manufacturing process of the athletic garment 130. By testing the athletic garment 130 before the athletic garment 130 is provided for an athlete's use, the exercise feedback system 100 reduces the likelihood that the athletic garment 130 will have a defect and thus, result in a poor user experience for the athlete. In this use case, the athletic garment 130 is not worn by the athlete during quality assurance, but rather on a manufacturing line or testing facility. Thus, the sensors measure impedance data instead of bioimpedance data. Two example processes for sensor quality assurance are described below.

FIG. 9A is a flowchart of a process 900 for testing for short circuits in a sensor-equipped athletic garment according to one embodiment. In some embodiments, the process 900 is performed by the exercise feedback system 100— e.g., modules of the exercise feedback system 100 described with reference to FIG. 4A—within the system environment in FIG. 1. The process 800 may include different or additional steps than those described in conjunction with FIG. 9A in some embodiments or perform steps in different orders than the order described in conjunction with FIG. 9A.

The bioimpedance module 410 receives 910 impedance data measured by a sensor of a sensor of an athletic garment 130. The bioimpedance module 410 determines 920 that the sensor has a short circuit if a magnitude value of the impedance data is less than a threshold value. During testing, the two electrodes of a non-defective sensor are not conductively coupled. Thus, the impedance measured by the non-defective sensor will be high, e.g., near or at an upper limit based on the biasing resistor 335 shown in FIGS. 3B-C. If the magnitude value is greater than the threshold value, e.g., a value less equivalent to half of the upper limit, the quality assurance module 440 determines that the sensor does not have a short circuit, i.e., the sensor is non-defective. Otherwise, the bioimpedance module 410 determines that the sensor has a short circuit because a lower impedance indicates that the electrodes of the sensor are conductively coupled, i.e., the sensor is defective. The quality assurance module 440 generates 930 a report, e.g., for a quality assurance test, identifying the sensor and indicating that the sensor includes a short circuit fault. The quality assurance module 440 may repeat the process 900 for each of the sensors of the athletic garment 130. The quality assurance module 440 may also generate a report aggregating the test results from each sensor. The report may indicate a pass or fail metric based on the number of sensors with a short circuit, e.g., the quality assurance module 440 generates a failing metric if the athletic garment 130 includes more than a threshold number of sensors with a short circuit.

FIG. 9B is a flowchart of a process 940 for testing for defective sensors in a sensor-equipped athletic garment according to one embodiment. In some embodiments, the process 940 is performed by the exercise feedback system 100—e.g., modules of the exercise feedback system 100 described with reference to FIG. 4A—within the system environment in FIG. 1. The process 940 may include different or additional steps than those described in conjunction with FIG. 9B in some embodiments or perform steps in different orders than the order described in conjunction with FIG. 9B.

The bioimpedance module 410 configures 950 a sensor of an athletic garment 130 to include a short circuit between two electrodes of the sensor. The bioimpedance module 410 receives 960 impedance data measured by the sensor of the athletic garment 130. The quality assurance module 440 determines 970 that the sensor is defective if a magnitude value of the impedance data is greater than a threshold value. In contrast to the process 900 for identifying sensors that have a short circuit, the exercise feedback system 100 may use the process 940 to test if any of the sensors measures incorrect impedance data. Since the sensor includes a short circuit, the magnitude value of the impedance data measured by the sensor should be low, that is, less than the threshold value. Thus, if the magnitude value of the impedance data is greater than the threshold value, the quality assurance module 440 determines that the sensor is defective. For instance, the sensor has a broken conductive trace between an electrode and the processing unit 290. The quality assurance module 440 generates 980 a report identifying the sensor and indicating that the sensor is defective. The quality assurance module 440 may repeat the process 940 for each of the sensors of the athletic garment 130.

IX. Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

The invention claimed is:

1. A method comprising:
receiving bioimpedance data from a garment worn by a user, the garment including a set of sensors configured to generate the bioimpedance data;
determining a first parameter value associated with a first sensor of the set of sensors, from the bioimpedance data generated by the first sensor, the first sensor associated with a first muscle;
determining a second parameter value associated with a second sensor of the set of sensors, from the bioimpedance data generated by the second sensor, the second sensor associated with a second muscle;
comparing the first parameter value and the second parameter value to a predetermined range; and
responsive to determining that the first parameter value is within the predetermined range indicating that the first sensor is in sufficient physical contact with the user and that the second parameter value is outside of the predetermined range indicating that the second sensor is not in sufficient physical contact with the user, providing a first metric indicative of performance of the first muscle for display but not providing a second metric indicative of performance of the second muscle.

2. The method of claim 1, further comprises:
determining, from the bioimpedance data generated by a third sensor, at least one of a shorted state of the third sensor and a broken state of an electrical pathway of the garment.

3. The method of claim 1, wherein determining the first parameter value and the second parameter value comprises determining a magnitude value of a sample of the bioimpedance data generated by a corresponding sensor and a variance value of the sample of the bioimpedance data.

4. The method of claim 1, further comprising:
performing a quality assurance test for the garment by determining an impedance parameter associated with the bioimpedance data from one or more sensors of the set of sensors, the impedance parameter derived from at least one of an impedance magnitude and a variation in impedance for electrical pathways of the garment based on a comparison of the impedance parameter to a threshold condition.

5. The method of claim 4, wherein performing the quality assurance test further comprises: based upon satisfaction of the threshold condition by the impedance magnitude, returning an indication of electrical pathway quality for each of the set of sensors of the garment.

6. The method of claim 4, wherein performing the quality assurance test comprises generating a report indicating a number of defective sensors that fail to satisfy respective threshold conditions.

7. The method of claim 4, further comprising:
providing a notification to a client device associated with the garment, based upon the quality assurance test, the notification indicating that one or more of the set of sensors is defective.

8. The method of claim 1, further comprising:
receiving physiological data from the garment generated by the second sensor, the physiological data describing muscle activation of the second muscle of the user while performing an exercise; and
modifying output of a metric associated with performance of the second muscle, in response to the second parameter value being outside of the predetermined range.

9. The method of claim 1, further comprising:
determining from the bioimpedance data, a number of sensors of the plurality of sensors that are not in sufficient physical contact with a portion of skin of the user.

10. A computer program product comprising a non-transitory computer readable storage medium having instructions encoded thereon that, when executed by a processor, cause the processor to:
receive bioimpedance data from a garment worn by a user, the garment including a set of sensors configured to generate bioimpedance data;
determine a first parameter value associated with a first sensor of the set of sensors, from the bioimpedance data generated by the first sensor, the first sensor associated with a first muscle;
determine a second parameter value associated with a second sensor of the set of sensors, from the bioimpedance data generated by the second sensor, the second sensor associated with a second muscle;
compare the first parameter value and the second parameter value to a predetermined range; and
responsive to determining that the first parameter value is within the predetermined range indicating that the first sensor is in sufficient physical contact with the user and that the second parameter value is outside of the predetermined range indicating that the second sensor is not in sufficient physical contact with the user, provide a first metric indicative of performance of the first muscle for display but not providing a second metric indicative of performance of the second muscle.

11. The computer program product of claim 10, having further instructions that when executed by the processor cause the processor to:
identify a sensor short circuit from the bioimpedance data generated by a third sensor.

12. The computer program product of claim 10, having further instructions that when executed by the processor cause the processor to generate a report indicating at least one of: a) a number of defective sensors that fail to satisfy respective threshold conditions and b) an indication of sensor quality for each of the set of sensors of the garment.

13. The computer program product of claim 10, having further instructions that when executed by the processor cause the processor to provide a notification to a client device associated with the garment, the notification indicating that one or more of the set of sensors is defective.

14. The method of claim 1, further comprising:
modifying a graphical user interface for display to the user via a client device, the graphical user interface including a depiction of muscles, wherein one or more muscles associated with parameter values outside of the predetermined range are applied with visual features to distinguish from one or more muscles associated with parameters values within the predetermined range.

15. The method of claim 14, further comprising:
determining, for each sensor of the set of sensors, a parameter value associated with a corresponding muscle;
comparing, for each sensor of the set of sensors, the parameter value to the predetermined range; and
responsive to determining that a number of sensors of the set of sensors associated with parameter values that are outside of the predetermined range is greater than a threshold, determining that the garment is defective; and
providing a notification to a client device associated with the user to inform the user that the garment is defective and that the garment should be replaced.

16. The method of claim 15, further comprising:
providing a size measurement of the user and the mailing address of the user to the client device associated with the user;
receiving a confirmation for a request to exchange from the client device; and
facilitating shipment of the new garment to the user.

17. The method of claim 15, further comprising:
responsive to receiving confirmation for a request from the user to replace the garment, retrieving user information indicating a mailing address of the user; and
generating a request to exchange the garment for a new garment based on a size measurement associated with the user.

18. The computer program product of claim 10, having further instructions that when executed by the processor cause the processor to modify a graphical user interface for display to the user via a client device, the graphical user interface including a depiction of muscles, wherein one or more muscles associated with parameter values outside of the predetermined range are applied with visual features to distinguish from one or more muscles associated with parameters values within the predetermined range.

19. The computer program product of claim 10, having further instructions that when executed by the processor cause the processor to:
determine, for each sensor of the set of sensors, a parameter value associated with a corresponding muscle;
compare, for each sensor of the set of sensors, the parameter value to the predetermined range;
responsive to determining that a number of sensors of the set of sensors associated with parameter values that are outside of the predetermined range is greater than a threshold, determine that the garment is defective; and
provide a notification to a client device associated with the user to inform the user that the garment is defective and that the garment should be replaced.

* * * * *